United States Patent [19]

Cherkofsky

[11] 4,379,159

[45] Apr. 5, 1983

[54] ANTIINFLAMMATORY 2-SUBSTITUTED-THIO-4,5-DIHYDRO-4,5-DIARYL-1H-IMIDAZOLES

[75] Inventor: Saul C. Cherkofsky, Wilmington, Del.

[73] Assignee: E. I. Du Pont de Nemours & Company, Wilmington, Del.

[21] Appl. No.: 197,750

[22] Filed: Oct. 16, 1980

[51] Int. Cl.$^3$ .................. A61K 31/415; C07D 233/28
[52] U.S. Cl. ................................ 424/273 R; 548/351
[58] Field of Search ..................... 424/273 R; 548/351

[56] References Cited

U.S. PATENT DOCUMENTS

4,190,666  2/1980  Cherkofsky .................. 424/274

FOREIGN PATENT DOCUMENTS

8073  2/1980  European Pat. Off. .

Primary Examiner—Stanley J. Friedman

[57] ABSTRACT

Antiinflammatory 2-substituted-thio-4,5-dihydro-4,5-diaryl-1H-imidazoles, such as 4,5-bis(4-chlorophenyl)-4,5-dihydro-2-(2,2,2-trifluoroethylthio)-1H-imidazole hydrochloride, useful for treatment of arthritis and related diseases.

15 Claims, No Drawings

ANTIINFLAMMATORY 2-SUBSTITUTED-THIO-4,5-DIHYDRO-4,5-DIARYL-1H-IMIDAZOLES

BACKGROUND OF THE INVENTION

This invention relates to antiinflammatory substituted-thio diaryl imidazoles.

2,3,5,6-Tetrahydro-6-phenylimidazole-[2,1-b]thiazole (Levamisole) has shown clinical efficacy as an antiarthritic. Levamisole was inactive in an adjuvant arthritis test, however, and its human efficacy is believed to be a result of its immunological activity.

2-Alkylthio-4-arylimidazolines are known in the literature. *J. Prakt. Chem.*, 318, 168 (1976) discloses 4,5-diphenyl-4,5-dihydro-1H-imidazole-2-thiol and its S-carboxymethyl derivative. U.S. Pat. No. 4,153,706 (Smith Kline) discloses 6-hydroxy-5,6-diaryl-2,3,5,6-tetrahydroimidazo[2,1-b]thiazoles and their antiarthritic activity.

There is a continuing need for safe and effective antiinflammatory agents. Inflammation is a disease process characterized by redness, fever, swelling and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as change in blood cells and central nervous system. Adreno-cortical steroids produce gastric irritation and suppression of normal adrenal function.

The present invention results from efforts to develop new antiarthritic compounds with good antiinflammatory activity and minimal side effects that could be more effective in treating arthritis than presently available drugs.

SUMMARY OF THE INVENTION

This invention relates to novel antiinflammatory compounds of formula I, pharmaceutical compositions containing them, and methods of using them to treat arthritis in mammals.

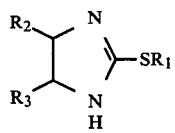

(I)

where
$R_1 = C_1-C_4$ alkyl, mono- or polyfluoro $C_2-C_4$ alkyl with the proviso that a fluoro group cannot be present in the α position, or allyl;
$R_2$ and $R_3$ independently =

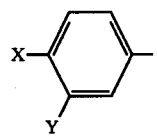

where
X=H, F, Cl, Br, $NO_2$ or $CH_3S(O)_n$; n=0, 1 or 2;
Y=H, F or Cl;

provided when Y=F or Cl, X must be F or Cl, and provided $R_2$ and $R_3$ cannot both be phenyl; or a pharmaceutically suitable acid addition salt thereof.

PREFERRED COMPOUNDS

Preferred compounds for utility considerations and/or ease of synthesis are where, independently:
$R_1$ = methyl or polyfluoro $C_2-C_3$ alkyl; or
$R_2$ and $R_3$ independently =

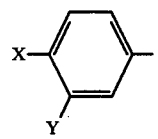

where X=F or Cl and Y=H.

An example of a preferred compound is 4,5-bis(4-chlorophenyl)-4,5-dihydro-2-(2,2,2-trifluoroethylthio)-1H-imidazole hydrochloride.

SYNTHESIS

Compounds of formula I can be prepared by reaction of an appropriate 4,5-diaryl-4,5-dihydro-1H-imidazole-2-thiol with an alkylating agent. Alkylating agents such as alkyl halides, sulfonates and dimethyl sulfate are considered to be within the context of this invention. The reaction is best carried out in a polar solvent such as acetone, methanol, ethanol or dimethylformamide at room temperature to the boiling point of the solvent.

Pharmaceutical salts of the compounds of formula I can be prepared by treatment of the free base I with an appropriate acid.

4,5-Diaryl-4,5-dihydro-1H-imidazole-2-thiols may be prepared by the reaction of carbon disulfide with an appropriate 1,2-diarylethylenediamine. Reactions of 1,2-diphenylethylenediamine with carbon disulfide to give 4,5-diphenyl-4,5-dihydro-1H-imidazole-2-thiol are described by J. A. Barth in *J. Prakt. Chem.*, 318, 168 (1976).

Syntheses of a variety of 1,2-diarylethylenediamines are described in S. Trippett, *J. Chem. Soc.* 4407 (1957), W. A. Sadler et al. *J. Chem. Soc. (Dalton Transactions)*, 1937 (1973) and F. Vogtle et al., *Chem. Ber.* 109, 1 (1976).

The compounds of this invention and their synthesis are illustrated further by the following examples. All temperatures are in degrees centigrade.

EXAMPLE 1

4,5-Bis(4-chlorophenyl)-4,5-dihydro-2-(methylthio)-1H-imidazole Hydrochloride A mixture of 12.2 g of 1,2-bis(4-chlorophenyl)ethylenediamine [*J. Chem. Soc.*, 4407 (1957)], 5 ml of carbon disulfide and 200 ml of ethanol was heated at reflux overnight. The solution was cooled and 7.6 g of 4,5-bis(4-chlorophenyl)-4,5-dihydro-1H-imidazole-2-thiol was collected by filtration. The colorless crystals had m.p. 209°–211°. The infrared and NMR spectra were consistent with this structure.

Anal. Calcd. for $C_{15}H_{12}N_2SCl_2$: C, 55.72; H, 3.71; N, 8.67. Found: C, 55.5; H, 4.27; N, 8.75.

A mixture of 8.0 g of 4,5-bis(4-chlorophenyl)-4,5-dihydro-1H-imidazole-2-thiol, 4.0 g of methyl iodide and 100 ml of ethanol was heated at reflux for 4 hours. The solvent was removed in vacuo and the residue distributed between methylene chloride and 10% aqueous NaHCO$_3$ solution. The organic layer was dried and evaporated to give 8.8 g of 4,5-bis(4-chlorophenyl)-4,5-dihydro-2-(methylthio)-1H-imidazole as a colorless oil. The NMR spectrum was consistent with this structure. The hydrochloride salt was prepared with dry hydrogen chloride gas in ether to give the title compound as colorless crystals (5.3 g), m.p. 236° dec.

Anal. Calcd. for C$_{16}$H$_{14}$N$_2$Cl$_2$S.HCl: C, 51.40; H, 4.02; N, 7.50. Found: C, 51.0; H, 4.31; N, 7.63.

EXAMPLE 2

4,5-Bis(4-chlorophenyl)-4,5-dihydro-2-(allylthio)-1H-imidazole Hydrochloride By the procedure described in Example 1, 2.0 g of 4,5-bis(4-chlorophenyl)-4,5-dihydro-1H-imidazole-2-thiol was converted to 1.0 g of the title compound with allyl bromide. After recrystallization from nitromethane, the colorless crystals had m.p. 208° dec. The infrared and NMR spectra of the free base were consistent with the proposed structure.

Anal. Calcd. for C$_{18}$H$_{16}$N$_2$SCl$_2$.HCl: C, 54.07; H, 4.25; N, 7.0. Found: C, 54.9; H, 4.53; N, 7.17.

EXAMPLE 3

4,5-Bis(4-chlorophenyl)-4,5-dihydro-2-(2,2,2-trifluoroethylthio)-1H-imidazole Hydrochloride By the procedure described in Example 1, 2.0 g of 4,5-bis-(4-chlorophenyl)-4,5-dihydro-1H-imidazole-2-thiol was reacted with 2,2,2-trifluoroethyl trichloromethanesulfonate to give the title compound. Recrystallization from nitromethane afforded 850 mg of colorless crystals, m.p. 230° dec. The NMR and infrared spectra were consistent with this structure.

Anal. Calcd. for C$_{17}$H$_{13}$F$_3$N$_2$Cl$_2$S.HCl: C, 46.22; H, 3.19; N, 6.34. Found: C, 46.8; H, 3.39; N, 6.63.

Additional compounds that can be prepared by the procedures illustrated in the examples are given in Table 1.

TABLE I

| R$_1$ | R$_2$ | R$_3$ |
|---|---|---|
| (CH$_2$)$_3$CH$_3$ | 4-FC$_6$H$_4$ | 4-FC$_6$H$_4$ |
| CH$_2$CF$_2$CH$_3$ | 4-BrC$_6$H$_4$ | 4-FC$_6$H$_4$ |
| (CH$_2$)$_2$CF$_3$ | 4-ClC$_6$H$_4$ | 4-NO$_2$C$_6$H$_4$ |
| CH$_2$CH$_3$ | 4-CH$_3$SC$_6$H$_4$ | 4-FC$_6$H$_4$ |
| CH$_3$ | 3,4-diClC$_6$H$_3$ | C$_6$H$_5$ |
| CH$_2$CH=CH$_2$ | 3-Cl, 4-FC$_6$H$_3$ | C$_6$H$_5$ |
| CH$_2$CF$_3$ | 3,4-diFC$_6$H$_3$ | C$_6$H$_5$ |
| (CH$_2$)$_3$CF$_3$ | 4-CH$_3$SOC$_6$H$_4$ | 4-FC$_6$H$_4$ |
| CH$_2$CF$_3$ | 4-CH$_3$SO$_2$C$_6$H$_4$ | 4-FC$_6$H$_4$ |

DOSAGE FORMS

The antiarthritic agents of this invention can be administered to treat arthritis by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. Ordinarily 0.05 to 50, and preferably 0.1 to 20 milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid; and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 75 milligrams of powdered active ingredient 150 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 75 milligrams of the active ingredient. The capsules are washed in petroleum ether and dried.

TABLETS

A large number of tablets are prepared by conventional procedures so that the dosage unit is 75 milligrams of active ingredient, 0.2 milligrams of colloidal silicon dioxide, 5 milligrams of magnesium stearate, 260 milligrams of microcrystalline cellulose, 11 milligrams of cornstarch and 88.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by filtration.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

INJECTABLE

A parenteral composition suitable for administration by injection is prepared by stirring 1% by weight of active ingredient in sodium chloride injection U.S.P. XV and sterilizing by filtration.

USE

To detect and compare the anti-inflammatory activities of compounds in this series and standard drugs, a test was used based on a standard model of arthritis for which there is good correlation with human efficacy. The model is adjuvant-induced arthritis in rats. Federation Proceedings, Vol. 32, No. 2, 1973, "Models Used for Study and Therapy of Rheumatoid Arthritis" —Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

Compounds of this invention have shown activity in adjuvant-induced arthritis in rats which is widely recognized as a good model of human rheumatoid arthritis.

METHODS

Established Adjuvant-Induced Arthritis in Rats

Lewis (Wistar) male rats (Charles River Breeding Laboratories, Wilmington, Mass.) weighing approximately 175–220 g were injected subcutaneously with 0.1 ml of adjuvant in the plantar area of the right hind paw. The adjuvant was prepared by bead-milling, heat-killed, lyophilized *Mycobacterium butyricum* (Difco #0640) in light mineral oil (Fisher Scientific Co. #0-119 Paraffin Oil— Saybolt Viscosity 125/135) 5 mg/ml. Twenty non-arthritic control rats were injected with mineral oil. The animals received water and Wayne Lab-Blox ad libitum*.

\* while on a 10-hour light–14 hour-dark cycle

The rats were held for 14 days to allow the development of polyarthritis. The volume of the uninjected, left-hind paw of each rat was measured by using a Ugo Basile Volume Differential Meter, Model 7101. Adjuvant injected rats showing no evidence of arthritis were discarded and the arthritic rats were distributed into groups of 10 having equal mean paw volumes with equal standard deviation. Non-arthritic (oil-injected) control rats were distributed to 2 groups of 10. Suspensions of test compounds were prepared for dosing by bead-milling (4 mm glass beads in rubber stoppered serum bottles) for 4–5 hours in aqueous 1% polyvinyl alcohol, 5% gum acacia and 0.5% methylparaben.

Test compounds were given orally by gavage once daily for 7 days (days 14–20). The 2 groups of oil injected, non-arthritic control rats and the 2 groups of arthritic control rats received vehicle only for 7 days. Paw volumes (uninjected left hind paw) were measured 20 hours after the last dose (on day 21).

Percent decrease from control mean paw volume was calculated with the following formula:

$$\frac{\text{Arthritic Vehicle Control Mean Paw Volume (ml)} - \text{Arthritic Treatment Mean Paw Volume (ml)}}{\text{Arthritic Vehicle Control Mean Paw Volume (ml)} - \text{Non-Arthritic Vehicle Control Mean Paw Volume (ml)}} \times 100 =$$

% Decrease from Control Mean Paw Volume

Dose-response regression lines of the % decrease were plotted on semi-log paper and the $ED_{50}\%$ for decrease from control paw volume was estimated by inspection.

TABLE II

| | RESULTS |
|---|---|
| Example | Adjuvant Arthritis $ED_{50}$ (mg/kg)[1] |
| 1 | 60 |
| 2 | (28%/25) |
| 3 | 25 |

[1]Values in parenthesis represent the percent reduction in paw volume at the indicated dose.

What is claimed is:
1. A compound of the formula

$$\underset{R_3}{\overset{R_2}{>}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!$$

where
$R_1 = C_1-C_4$ alkyl, mono- or polyfluoro $C_2-C_4$ alkyl with the proviso that a fluoro group cannot be present in the $\alpha$ position, or allyl;
$R_2$ and $R_3$ independently =

(benzene ring with substituents X and Y)

where
$X = H$, F, Cl, Br, $NO_2$ or $CH_3S(O)_n$; $n = 0$, 1 or 2;
$Y = H$, F or Cl;

provided when Y=F or Cl, X must be F or Cl, and provided $R_2$ and $R_3$ cannot both be phenyl; or a pharmaceutically suitable acid addition salt thereof.

2. A compound of claim 1 where $R_1$=methyl or polyfluoro $C_2$-$C_3$ alkyl.

3. A compound of claim 1 where $R_2$ and $R_3$ independently=

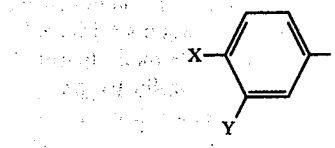

where X=F or Cl and Y=H.

4. A compound of claim 3 where $R_1$=methyl or polyfluoro $C_2$-$C_3$ alkyl.

5. The compound of claim 1 which is 4,5-bis(4-chlorophenyl)-4,5-dihydro-2-(2,2,2-trifluoroethylthio)-1H-imidazole hydrochloride.

6. A pharmaceutical composition consisting essentially of a suitable pharmaceutical carrier and an effective antiinflammatory amount of a compound of claim 1.

7. A pharmaceutical composition consisting essentially of a suitable pharmaceutical carrier and an effective antiinflammatory amount of a compound of claim 2.

8. A pharmaceutical composition consisting essentially of a suitable pharmaceutical carrier and an effective antiinflammatory amount of a compound of claim 3.

9. A pharmaceutical composition consisting essentially of a suitable pharmaceutical carrier and an effective antiinflammatory amount of a compound of claim 4.

10. A pharmaceutical composition consisting essentially of a suitable pharmaceutical carrier and an effective antiinflammatory amount of the compound of claim 5.

11. A method of treating inflammation in a mammal which comprises administering to the mammal an effective antiinflammatory amount of a compound of claim 1.

12. A method of treating inflammation in a mammal which comprises administering to the mammal an effective antiinflammatory amount of a compound of claim 2.

13. A method of treating inflammation in a mammal which comprises administering to the mammal an effective antiinflammatory amount of a compound of claim 3.

14. A method of treating inflammation in a mammal which comprises administering to the mammal an effective antiinflammatory amount of a compound of claim 4.

15. A method of treating inflammation in a mammal which comprises administering to the mammal an effective antiinflammatory amount of the compound of claim 5.

* * * * *